Figure 1:
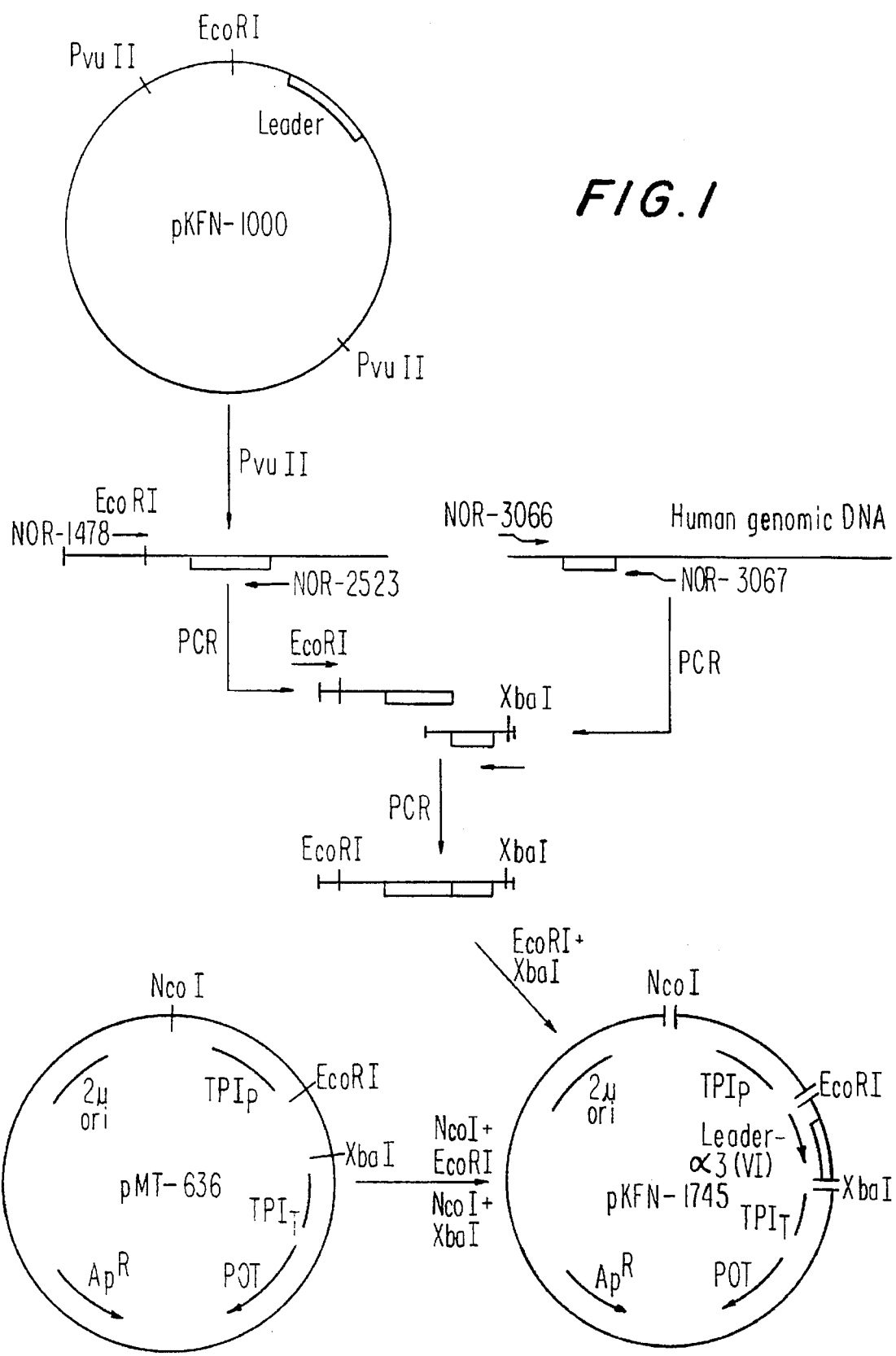

United States Patent [19]

Bjørn et al.

[11] Patent Number: 5,629,176
[45] Date of Patent: May 13, 1997

[54] HUMAN KUNITZ-TYPE PROTEASE INHIBITOR VARIANTS

[75] Inventors: Søren E. Bjørn, Lyngby; Kjeld Norris; Fanny Norris, both of Hellerup; Lars C. Petersen, Hørsholm; Ole H. Olsen, Brønshøj, all of Denmark

[73] Assignee: Novo Nordisk A/S, Bagsvaerd, Denmark

[21] Appl. No.: 334,773

[22] Filed: Nov. 4, 1994

Related U.S. Application Data

[63] Continuation of Ser. No. 26,135, filed as PCT/DK93/00002, Jan. 7, 1993, abandoned.

[51] Int. Cl.⁶ .................. C12P 21/06; C12N 1/20; A61K 38/00; C07K 1/00
[52] U.S. Cl. .................. 435/69.2; 435/69.1; 435/172.3; 435/254.3; 435/252.3; 435/254.11; 435/320.1; 435/254.2; 435/254.21; 435/325; 435/365; 435/358; 514/12; 530/300; 530/324; 530/356; 536/23.5; 930/250
[58] Field of Search .................. 435/69.1, 69.2, 435/172.3, 240.2, 252.3, 255, 320.1; 514/12; 530/300, 324, 356; 536/23.5; 930/250

[56] References Cited

U.S. PATENT DOCUMENTS

5,278,285 1/1994 Ebbers et al. .................. 435/69.2

FOREIGN PATENT DOCUMENTS

0393431 4/1989 European Pat. Off. .
0401508 5/1990 European Pat. Off. .

OTHER PUBLICATIONS

Chemical Abstracts No. 147399x, vol. 113, No. 17 (Oct. 22, 1990), p. 289.
Larvin et al "Intra–Peritoneal Aprotinin Therapy for Acute Paucueatitis", *Bio. Chem. Hoppe Seyer* 369 (*Suppl*): 149–152 (May 1988).

Brinkmann et al, "Recombinant aprotinin . . . " *Eur. J. Biochem* 202:95–99 (1991).

Schulz et al, "*Principles of Protein Structure*", pp. 14–16 (1979).

Bonaldo et al, "The Carboxyl Terminus of the Chicken α 3 chain of Collagen VI . . . ", *J. Biol. Chem.* 264(34):20235–20239, (Dec. 1989).

Chu et al, "Mosaic Structure of . . . human type VI collagen α 3 chainin" *The EMBO J* 9(2):385–393 (1990).

Broze et al, "Regulation of Coagulation . . . " Biochem 29(33):7539–7546 (Aug. 1990).

*Primary Examiner*—Robert A. Wax
*Assistant Examiner*—Hyosuk Kim
*Attorney, Agent, or Firm*—Steve T. Zelson, Esq.; Cheryl H. Agris, Esq.

[57] ABSTRACT

A variant of the C-terminal Kunitz-type protease inhibitor domain of the α3 chain of human type VI collagen, the variant comprising the following amino acid sequence $X^1$ $X^{16}$ Asp Ile Cys Lys Leu Pro Lys Asp $X^2$ Gly $X^3$ Cys $X^4$ $X^5$ $X^6$ $X^7$ $X^8$ $X^9$ Trp Tyr Tyr Asp Pro Asn Thr Lys Ser Cys Ala Arg Phe $X^{10}$ Tyr Gly Gly Cys $X^{11}$ $X^{12}$ $X^{13}$ Glu Asn Lys Phe $X^{14}$ Ser Gln Lys Glu Cys Glu Lys Val Cys Ala Pro $X^{15}$ (SEQ ID NO. 1) wherein $X^1$, $X^{15}$, and $X^{16}$ represents a naturally occurring amino acid residues except Cys and $X^2$–$X^{14}$ each independently respresents a naturally occurring amino acid residue, with the proviso that at least one of the amino acid residues $X^1$–$X^{16}$ is different from the corresponding amino acid residue of the native sequence. Alternatively, the N-terminal Asp may be preceded by H or 3–5 amino acid residues and the C-terminal Pro may be followed by OH or 3–5 amino acid residues.

9 Claims, 1 Drawing Sheet

HUMAN KUNITZ-TYPE PROTEASE INHIBITOR VARIANTS

This is a continuation of application PCT/DK93/00002, filed on Jan. 7, 1993 which is a continuation application of application Ser. No. 08/026,135, filed Feb. 24, 1993, now abandoned the contents of which are incorporated herein by reference.

FIELD OF INVENTION

The present invention relates to a variant of a human Kunitz-type protease inhibitor domain, DNA encoding the variant, a method of producing the variant and a pharmaceutical composition containing the variant.

BACKGROUND OF THE INVENTION

Polymorphonuclear leukocytes (neutrophils or PMNs) and mononuclear phagocytes (monocytes) play an important part in tissue injury, infection, acute and chronic inflammation and wound healing. The cells migrate from the blood to the site of inflammation and, following appropriate stimulation, they release oxidant compounds ($O_2.$, $O_2$—, $H_2O_2$ and HOCl) as well as granules containing a variety of proteolytic enzymes. The secretory granules contain, i.a., alkaline phosphatase, metalloproteinases such as gelatinase and collagenase and serine proteases such as neutrophil elastase, cathepsin G and proteinase 3.

Latent metalloproteinases are released together with tissue inhibitor of metalloproteinase (TIMP). The activation mechanism has not been fully elucidated, but it is likely that oxidation of thiol groups and/or proteolysis play a part in the process. Also, free metalloproteinase activity is dependent on inactivation of TIMP.

In the azurophil granules of the leukocytes, the serine proteases neutrophil elastase, cathepsin G and proteinase-3 are packed as active enzymes complexed with glucosaminoglycans. These complexes are inactive but dissociate on secretion to release the active enzymes. To neutralize the protease activity, large amounts of the inhibitors $\alpha_1$-proteinase inhibitor ($\alpha_1$-PI) and $\alpha_1$-chymotrypsin inhibitor ($\alpha_1$-ChI) are found in plasma. However, the PMNs are able to inactivate the inhibitors locally. Thus, $\alpha_1$-PI which is the most important inhibitor of neutrophil elastase is sensitive to oxidation at the reactive center (Met-358) by oxygen metabolites produced by triggered PMNs. This reduces the affinity of $\alpha_1$-PI for neutrophil elastase by approximately 2000 times.

After local neutralization of $\alpha_1$-PI, the elastase is able to degrade a number of inhibitors of other proteolytic enzymes. Elastase cleaves $\alpha_1$-ChI and thereby promotes cathepsin G activity. It also cleaves TIMP, resulting in tissue degradation by metalloproteinases. Furthermore, elastase cleaves antithrombin III and heparin cofactor II, and tissue factor pathway inhibitor (TFPI) which probably promotes clot formation. On the other hand, the ability of neutrophil elastase to degrade coagulation factors is assumed to have the opposite effect so that the total effect of elastase is unclear. The effect of neutrophil elastase on fibrinolysis is less ambiguous. Fibrinolytic activity increases when the elastase cleaves the plasminogen activator inhibitor and the $\alpha_2$ plasmin inhibitor. Besides, both of these inhibitors are oxidated and inactivated by $O_2$ metabolites.

PMNs contain large quantities of serine proteases, and about 200 mg of each of the leukocyte proteases are released daily to deal with invasive agents in the body. Acute inflammation leads to a many-fold increase in the amount of enzyme released. Under normal conditions, proteolysis is kept at an acceptably low level by large amounts of the inhibitors $\alpha_1$-PI, $\alpha_1$-ChI and $\alpha_2$ macroglobulin. There is some indication, however, that a number of chronic diseases is caused by pathological proteolysis due to overstimulation of the PMNs, for instance caused by autoimmune response, chronic infection, tobacco smoke or other irritants, etc.

Aprotinin (bovine pancreatic trypsin inhibitor) is known to inhibit various serine proteases, including trypsin, chymotrypsin, plasmin and kallikrein, and is used therapeutically in the treatment of acute pancreatitis, various states of shock syndrome, hyperfibrinolytic hemorrhage and myocardial infarction (ycf., for instance, J. E. Trapnell et al, *Brit. J. Surg.* 61, 1974, p. 177; J. McMichan et al., *Circulatory shock* 9, 1982, p. 107; L. M. Auer et al., *Acta Neurochir.* 49, 1979, p. 207; G. Sher, *Am. J. Obstet. Gynecol.* 129, 1977, p. 164; and B. Schneider, *Artzneim.-Forsch.* 26, 1976, p. 1606). Administration of aprotinin in high doses significantly reduces blood loss in connection with cardiac surgery, including cardiopulmonary bypass operations (cf., for instance, B. P. Bidstrup et al., *J. Thorac. Cardiovasc. Surg.* 97, 1989, pp. 364–372; W. van Oeveren et al., *Ann. Thorac. Surg.* 44, 1987, pp. 640–645). It has previously been demonstrated (cf. H. R. Wenzel and H. Tschesche, *Angew. Chem. Internat. Ed.* 20, 1981, p. 295) that certain aprotinin analogues, e.g. aprotinin(1–58, Val15) exhibit a relatively high selectivity for granulocyte elastase and an inhibitory effect on collagenase. Aprotinin (1–58, Ala15) has a weak effect on elastase, while aprotinin (3–58, Arg15, Ala17, Ser42) exhibits an excellent plasma kallikrein inhibitory effect (cf. WO 89/10374).

However, when administered in vivo, aprotinin has been found to have a nephrotoxic effect in rats, rabbits and dogs after repeated injections of relatively high doses of aprotinin (Bayer, *Trasylol, Inhibitor of proteinase;* E. Glaser et al. in "Verhandlungen der Deutschen Gesellschaft für Innere Medizin, 78. Kongress", Bergmann, München, 1972, pp. 1612–1614). The nephrotoxicity (i.a. appearing in the form of lesions) observed for aprotinin might be ascribed to the accumulation of aprotinin in the proximal tubulus cells of the kidneys as a result of the high positive net charge of aprotinin which causes it to be bound to the negatively charged surfaces of the tubuli. This nephrotoxicity makes aprotinin less suitable for clinical purposes, in particular those requiring administration of large doses of the inhibitor (such as cardiopulmonary bypass operations). Besides, aprotinin is a bovine protein which may therefore contain one or more epitopes which may give rise to an undesirable immune response on administration of aprotinin to humans.

It is therefore an object of the present invention to identify human protease inhibitors of the same type as aprotinin (i.e. Kunitz-type inhibitors) with a similar inhibitor profile or modified to exhibit a desired inhibitor profile.

SUMMARY OF THE INVENTION

The present invention relates to a variant of the C-terminal Kunitz-type protease inhibitor domain of the α3 chain of human type VI collagen, the variant comprising the following amino acid sequence $X^1$ $X^{16}$ Asp Ile Cys Lys Leu Pro Lys Asp $X^2$ Gly $X^3$ Cys $X^4$ $X^5$ $X^6$ $X^7$ $X^8$ $X^9$ Trp Tyr Tyr Asp Pro Asn Thr Lys Ser Cys Ala Arg Phe $X^{10}$ Tyr Gly Gly Cys $X^{11}$ $X^{12}$ $X^{13}$ Glu Asn Lys Phe $X^{14}$ Ser Gln Lys Glu Cys Glu Lys Val Cys Ala Pro $X^{15}$ (SEQ ID NO. 1) wherein $X^1$, $X^{15}$, and $X^{16}$ represents a naturally occurring amino acid residues except Cys and $X^2$–$X^{14}$ each independently represents a naturally occurring amino acid residue, with the proviso that at least one of the amino acid residues $X^1$–$X^{16}$ is different from the corresponding amino acid residue of the native sequence. Alternatively, the N-terminal Asp may be preceded by H or 3–5 amino acid residues and the C-terminal Pro may be followed by OH or 3–5 amino acid residues.

In the present context, the term "naturally occurring amino acid residue" is intended to indicate any one of the 20 commonly occurring amino acids, i.e. Ala, Val, Leu, Ile Pro, Phe, Trp, Met, Gly, Ser, Thr, Cys, Tyr, Asn, Gln, Asp, Glu, Lys, Arg and His.

Human type VI collagen has been described by R. Timpl and J. Engel (1987), in K. Mayne and R. E. Burgeson (Eds.), *Structure and Function of Collagen Types*, Academic Press, Orlando, Fla., pp. 105–143, and the cDNA coding for the protein has been cloned, cf. M.-L. Chu et al., *The EMBO J.* 9, 1990, pp. 385–393. Analysis of the primary structure of the protein has shown that the α3 chain of the protein includes a Kunitz-type inhibitor domain at the C-terminal end from amino acid 2874 to amino acid 2931.

By substituting one or more amino acids in one or more of the positions indicated above, it may be possible to change the inhibitor profile of this Kunitz-type domain (in the following referred to as the α3 VI Kunitz-type domain) so that it preferentially inhibits neutrophil elastase, cathepsin G and/or proteinase-3. Furthermore, it may be possible to construct variants which specifically inhibit enzymes involved in coagulation or fibrinolysis (e.g. plasmin or plasma kallikrein) or the complement cascade.

One advantage of the α3 VI Kunitz-type domain is that it has a zero net charge as opposed to aprotinin which, as indicated above, has a strongly positive net charge. It is therefore possible to construct variants of the invention with a lower positive net charge than aprotinin, thereby reducing the risk of kidney damage on administration of large doses of the variants. Another advantage is that, contrary to aprotinin, it is a human protein (fragment) so that undesired immunological reactions on administration to humans are significantly reduced.

BRIEF DESCRIPTION OF THE DRAWINGS

FIG. 1 shows the construction of plasmid pKFN-1745.

DETAILED DISCLOSURE OF THE INVENTION

Examples of preferred variants of the α3 VI Kunitz-type domain are variants wherein $X^1$ is Glu; $X^{16}$ is Thr; or wherein $X^2$ is an amino acid residue selected from the group consisting of Ala, Arg, Thr, Asp, Pro, Glu, Lys, Gln, Ser, Ile and Val, in particular wherein $X^2$ is Thr or Glu; or wherein $X^3$ is an amino acid residue selected from the group consisting of Pro, Thr, Leu, Arg, Val and Ile, in particular wherein $X^3$ is Pro or Thr; or wherein $X^4$ is an amino acid residue selected from the group consisting of Lys, Arg, Val, Thr, Ile, Leu, Phe, Gly, Ser, Met, Trp, Tyr, Gln, Asn and Ala, in particular wherein $X^4$ is Lys, Val, Leu, Ile, Thr, Met, Gln or Arg; or wherein $X^5$ is an amino acid residue selected from the group consisting of Ala, Gly, Thr, Arg, Phe, Gln and Asp, in particular wherein $X^5$ is Ala, Thr, Asp or Gly; or wherein $X^6$ is an amino acid residue selected from the group consisting of Arg, Ala, Lys, Leu, Gly, His, Ser, Asp, Gln, Glu, Val, Thr, Tyr, Phe, Asn, Ile and Met, in particular wherein $X^6$ is Arg, Phe, Ala, Leu or Tyr; or wherein $X^7$ is an amino acid residue selected from the group consisting of Ile, Met, Gln, Glu, Thr, Leu, Val and Phe, in particular wherein $X^7$ is Ile; or wherein $X^8$ is an amino acid residue selected from the group consisting of Ile, Thr, Leu, Asn, Lys, Ser, Gln, Glu, Arg, Pro and Phe, in particular wherein $X^8$ is Ile or Leu; or wherein $X^9$ is an amino acid residue selected from the group consisting of Arg, Ser, Ala, Gln, Lys and Leu, in particular wherein $X^9$ is Lys or Arg; or wherein $X^{10}$ is an amino acid residue selected from the group consisting of Gln, Pro, Phe, Ile Lys, Trp, Ala, Thr, Leu, Ser, Tyr, His, Asp, Met, Arg and Val, in particular wherein $X^{10}$ is Val or Trp; or wherein $X^{11}$ is an amino acid residue selected from the group consisting of Gly, Met, Gln, Glu, Leu, Arg, Lys, Pro and Asn, in particular wherein $X^{11}$ is Arg or Gly; or wherein $X^{12}$ is Ala or Gly; or wherein $X^{13}$ is an amino acid residue selected from the group consisting of Lys, Asn and Asp, in particular wherein $X^{13}$ is Lys or Asn; or wherein $X^{14}$ is an amino acid residue selected from the group consisting of Val, Tyr, Asp, Glu, Thr, Gly, Leu, Ser, Ile, Gln, His, Asn, Pro, Phe, Met, Ala, Arg, Trp and Lys, in particular wherein $X^{14}$ is Lys or Gly; or wherein $X^{15}$ is Val. In a preferred embodiment, $X^1$ is Glu, $X^{16}$ is Thr, and $X^{15}$ is Val, while $X^2$–$X^{14}$ are as defined above.

Variants of the α3 VI Kunitz-type domain of the invention should preferably not contain a Met residue in the protease binding region (i.e. the amino acid residues represented by $X^3$–$X^{14}$). By analogy to α1-PI described above, a Met residue in any one of these positions would make the inhibitor sensitive to oxidative inactivation by oxygen metabolites produced by PMNs, and conversely, lack of a Met residue in these positions should render the inhibitor more stable in the presence of such oxygen metabolites.

A currently preferred variant of the invention is one in which one or more of the amino acid residues located at the protease-binding site of the Kunitz domain (i.e. one or more of $X^3$–$X^{14}$ corresponding to positions 13, 15, 16, 17, 18, 19, 20, 34, 39, 40, 41 and 46 of aprotinin) are substituted to the amino acids present in the same positions of native aprotinin. This variant comprises the following amino acid sequence Glu Thr Asp Ile Cys Lys Leu Pro Lys Asp Glu Gly Pro Cys Lys Ala Arg Ile Ile Arg Trp Tyr Tyr Asp Pro Asn Thr Lys Ser Cys Ala Arg Phe Val Tyr Gly Gly Cys Arg Ala Lys Glu Asn Lys Phe Lys Ser Gln Lys Glu Cys Glu Lys Val Cys Ala Pro Val (SEQ ID No. 2).

In another aspect, the invention relates to a DNA construct encoding a human Kunitz-type inhibitor domain variant according to the invention. The DNA construct of the invention may be prepared synthetically by established standard methods, e.g. the phosphoamidite method described by S. L. Beaucage and M. H. Caruthers, *Tetrahedron Letters* 22, 1981, pp. 1859–1869, or the method described by Matthes et al., *EMBO Journal* 3, 1984, pp. 801–805. According to the phosphoamidite method, oligonucleotides are synthesized, e.g. in an automatic DNA synthesizer, purified, annealed, ligated and cloned in suitable vectors.

Alternatively, it is possible to use genomic or cDNA coding for the α3 VI Kunitz-type domain (e.g. obtained by screening a genomic or cDNA library for DNA coding for type VI collagen using synthetic oligonucleotide probes and isolating the DNA sequence coding for the Kunitz-type domain therefrom). The DNA sequence is modified at one or more sites corresponding to the site(s) at which it is desired to introduce amino acid substitutions, e.g. by site-directed mutagenesis using synthetic oligonucleotides encoding the desired amino acid sequence for homologous recombination in accordance with well-known procedures.

In a still further aspect, the invention relates to a recombinant expression vector which comprises a DNA construct of the invention. The recombinant expression vector may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

In the vector, the DNA sequence encoding the α3 VI Kunitz-type domain variant of the invention should be operably connected to a suitable promoter sequence. The promoter may be any DNA sequence which shows transcriptional activity in the host cell of choice and may be derived from genes encoding proteins either homologous or heterologous to the host cell. Examples of suitable promoters for directing the transcription of the DNA encoding the α3 VI Kunitz-type domain variant of the invention in mammalian cells are the SV 40 promoter (Subramani et al., *Mol. Cell Biol.* 1, 1981, pp. 854–864), the MT-1 (metallothionein gene) promoter (Palmiter et al., *Science* 222, 1983, pp. 809–814) or the adenovirus 2 major late promoter. Suitable promoters for use in yeast host cells include promoters from yeast glycolytic genes (Hitzeman et al., *J. Biol. Chem.* 255, 1980, pp. 12073–12080; Alber and Kawasaki, *J. Mol. Appl. Gen.* 1, 1982, pp. 419–434) or alcohol dehydrogenase genes (Young et al., in *Genetic Engineering of Microorganisms for Chemicals* (Hollaender et al, eds.), Plenum Press, New York, 1982), or the TPI1 (U.S. Pat. No. 4,599,311) or ADH2-4c (Russell et al., *Nature* 304, 1983, pp. 652–654) promoters. Suitable promoters for use in filamentous fungus host cells are, for instance, the ADH3 promoter (McKnight et al., *The EMBO J.* 4, 1985, pp. 2093–2099) or the tpiA promoter.

The DNA sequence encoding the α3 VI Kunitz-type domain variant of the invention may also be operably connected to a suitable terminator, such as the human growth hormone terminator (Palmiter et al., op. cit.) or (for fungal hosts) the TPI1 (Alber and Kawasaki, op. cit.) or ADH3 (McKnight et al., op. cit.) promoters. The vector may further comprise elements such as polyadenylation signals (e.g. from SV 40 or the adenovirus 5 Elb region), transcriptional enhancer sequences (e.g. the SV 40 enhancer) and translational enhancer sequences (e.g. the ones encoding adenovirus VA RNAs).

The recombinant expression vector of the invention may further comprise a DNA sequence enabling the vector to replicate in the host cell in question. An example of such a sequence (when the host cell is a mammalian cell) is the SV 40 origin of replication, or (when the host cell is a yeast cell) the yeast plasmid 2µ replication genes REP 1–3 and origin of replication. The vector may also comprise a selectable marker, e.g. a gene the product of which complements a defect in the host cell, such as the gene coding for dihydrofolate reductase (DHFR) or one which confers resistance to a drug, e.g. neomycin, hygromycin or methotrexate, or the *Schizosaccharomyces pombe* TPI gene (described by P. R. Russell, Gene 40, 1985, pp. 125–130).

The procedures used to ligate the DNA sequences coding for the α3 VI Kunitz-type domain variant of the invention, the promoter and the terminator, respectively, and to insert them into suitable vectors containing the information necessary for replication, are well known to persons skilled in the art (cf., for instance, Sambrook et al., *Molecular Cloning: A Laboratory Manual*, Cold Spring Harbor, New York, 1989).

The host cell into which the expression vector of the invention is introduced may be any cell which is capable of producing the α3 VI Kunitz-type domain variant of the invention and is preferably a eukaryotic cell, such as a mammalian, yeast or fungal cell.

The yeast organism used as the host cell according to the invention may be any yeast organism which, on cultivation, produces large quantities of the α3 VI Kunitz-type domain variant of the invention. Examples of suitable yeast organisms are strains of the yeast species *Saccharomyces cerevisiae*, *Saccharomyces kluyveri*, *Schizosaccharomyces pombe* or *Saccharomyces uvarum*. The transformation of yeast cells may for instance be effected by protoplast formation followed by transformation in a manner known per se.

Examples of suitable mammalian cell lines are the COS (ATCC CRL 1650), BHK (ATCC CRL 1632, ATCC CCL 10) or CHO (ATCC CCL 61) cell lines. Methods of transfecting mammalian cells and expressing DNA sequences introduced in the cells are described in e.g. Kaufman and Sharp, *J. Mol. Biol.* 159, 1982, pp. 601–621; Southern and Berg, *J. Mol. Appl. Genet.* 1, 1982, pp. 327–341; Loyter et al., *Proc. Natl. Acad. Sci. USA* 79, 1982, pp. 422–426; Wigler et al., *Cell* 14, 1978, p. 725; Corsaro and Pearson, *Somatic Cell Genetics* 7, 1981, p. 603, Graham and van der Eb, *Virology* 52, 1973, p. 456; and Neumann et al., *EMBO J.* 1, 1982, pp. 841–845.

Alternatively, fungal cells may be used as host cells of the invention. Examples of suitable fungal cells are cells of filamentous fungi, e.g. Aspergillus spp. or Neurospora spp., in particular strains of *Aspergillus oryzae* or *Aspergillus niger*. The use of Aspergillus spp. for the expression of proteins is described in, e.g., EP 238 023.

The present invention further relates to a method of producing an α3 VI Kunitz-type domain variant according to the invention, the method comprising culturing a cell as described above under conditions conducive to the expression of the variant and recovering the resulting variant from the culture.

The medium used to cultivate the cells may be any conventional medium suitable for growing mammalian cells or fungal (including yeast) cells, depending on the choice of host cell. The variant will be secreted by the host cells to the growth medium and may be recovered therefrom by conventional procedures including separating the cells from the medium by centrifugation or filtration, precipitating the proteinaceous components of the supernatant or filtrate by means of a salt, e.g. ammonium sulfate, purification by a variety of chromatographic procedures, e.g. ion exchange chromatography or affinity chromatography, or the like.

The present invention also relates to a pharmaceutical composition comprising an α3 VI Kunitz-type domain variant of the invention together with a pharmaceutically acceptable carrier or excipient. In the composition of the invention, the variant may be formulated by any of the established methods of formulating pharmaceutical compositions, e.g. as described in *Remington's Pharmaceutical Sciences*, 1985. The composition may typically be in a form suited for systemic injection or infusion and may, as such, be formulated with sterile water or an isotonic saline or glucose solution.

The α3 VI Kunitz-type domain II variant of the invention is therefore contemplated to be advantageous to use for the therapeutic applications suggested for native aprotinin or aprotinin analogues with other inhibitor profiles, in particular those which necessitate the use of large aprotinin doses.

Therapeutic applications for which the use of the variant of the invention is indicated as a result of its ability to inhibit human serine proteases, e.g. trypsin, plasmin, kallikrein, elastase, cathepsin G and proteinase-3, include (but are not limited to) acute pancreatitis, inflammation, thrombocytopenia, preservation of platelet function, organ preservation, wound healing, shock (including shock lung) and conditions involving hyperfibrinolytic haemorrhage, emphysema, rheumatoid arthritis, adult respiratory distress syndrome, chronic inflammatory bowel disease and psoriasis, in other words diseases presumed to be caused by pathological proteolysis by elastase, cathepsin G and proteinase-3 released from triggered PMNs.

Furthermore, the present invention relates to the use of the α3 VI Kunitz-type inhibitor domain or a variant thereof as described above for the preparation of a medicament for the prevention or therapy of diseases or conditions associated with pathological proteolysis by proteases released from overstimulated PMNs. As indicated above, it may be an advantage of administer heparin concurrently with the α3 VI Kunitz-type inhibitor domain or variant.

Apart from the pharmaceutical use indicated above, the α3 VI Kunitz-type inhibitor domain or a variant thereof as specified above may be used to isolate useful natural substances, e.g. proteases or receptors from human material, which bind directly or indirectly to the α3 VI Kunitz-type inhibitor domain, for instance by screening assays or by affinity chromatography.

The invention is described in further detail in the following examples which are not in any way intended to limit the scope of the invention as claimed.

EXAMPLES

General Methods.

Standard DNA techniques were carried out as described (Sambrook, J., Fritch, E. F., and Maniatis, T. (1982) Molecular Cloning: A Laboratory Manual, Cold Spring Harbor Laboratory Press, Cold Spring Harbor, N.Y.). Synthetic oligonucleotides were prepared on an automatic DNA synthesizer (380B, Applied Biosystems) using phosphoramidite chemistry on a controlled pore glass support (Beaucage, S. L., and Caruthers, M. H., Tetrahedron Letters 22, (1981) 1859–1869). DNA sequence determinations were performed by the dideoxy chain-termination technique (Sanger, F., Micklen, S., and Coulson, A. R., Proc. Natl. Acad. Sci. USA 74 (1977) 5463–5467). Polymerase chain reactions (PCR) were performed on a DNA Thermal Cycler (Perkin Elmer Cetus).

Amino acid analysis was carried out after hydrolysis in 6M HCl at 110° C. in vacuum-sealed tubes for 24 hours. Analysis was performed on a Beckman 121MB automatic amino acid analyzer modified for microbore operation.

N-terminal amino acid sequence analysis was obtained by automated Edman degradation using an Applied Biosystems 470A gas-phase sequencer. Analysis by on-line reverse phase HPLC was performed for the detection and quantitation of the liberated PTH amino acids from each sequencer cycle.

Molecular weight determination was obtained on a BIO-ION 20 plasma desorption mass spectrometer (PDMS) equipped with a flight tube of approximately 15 cm and operated in positive mode. Aliquots of 5 μl were analyzed at an accelerating voltage set to 15 kV and ions were collected for 5 million fission events. The accuracy on assigned molecular ions is approximately 0.1% for well defined peaks, otherwise somewhat less.

Example 1

Production of Human α3(VI) Kunitz-type Protease Inhibitor Domain from Yeast Strain KFN-1758

1 μg of human genomic DNA (Clontech, Palo Alto, Calif., U.S.A., cat. no. 6550-2 was used as a template in a PCR reaction containing 100 pmole each of the primers NOR-3067 (GACGGATCTAGATTACACAGGAGCGCAAACC TTTTCACA) (SEQ ID No. 7) and NOR-3066 (GCTGAGAGATTGGAGAAGAGAGAAACAGATATAT GCAAGTTGCC) (SEQ ID No. 8). NOR-3067 is complementary to bases no. 9100–9123 in the cDNA sequence of human α3(VI) collagen (Chu, M-L., Zhang, R-Z., Pan, T-C., Stokes, D., Conway, D., Kuo, H-J., Glanville, R., Mayer, U., Mann, K., Denzmann, R., and Timpl, R. EMBO J. 9 (1990) 385–393) and carries a 5' extension containing a translation stop codon followed by an XbaI site. The 23 3'-terminal bases of NOR-3066 are identical to bases 8950 to 8972 in the cDNA sequence of human α3(VI) collagen and the 21 5'-terminal bases of NOR-3066 are identical to bases 215 to 235 in the synthetic leader gene (see SEQ ID No. 3) from pKFN-1000 described below.

The PCR reaction was performed in a 100 μl volume using a commercial kit (GeneAmp, Perkin Elmer Cetus) and the following cycle: 94° for 20 sec, 50° for 20 sec, and 72° for 30 sec. After 19 cycles a final cycle was performed in which the 72° step was maintained for 10 min. The PCR product, a 210 bp fragment, was isolated by electrophoresis on a 2% agarose gel.

Signal-leader: 0.1 μg of a 0.7 kb PvuII fragment from pKFN-1000 described below was used as a template in a PCR reaction containing 100 pmole each of the primers NOR-1478 (GTAAAACGACGGCCAGT) (SEQ ID No. 9) and NOR-2523 (TCTCTTCTCCAATCTCTCAGC) (SEQ ID No. 10). NOR-1478 is matching a sequence just upstream of the EcoRI site in SEQ ID No. 3. Primer NOR-2523 is complementary to the 17 3'-terminal bases of the synthetic leader gene of pKFN-1000, see FIG. 1. The PCR reaction was performed as described above, resulting in a 257 bp fragment.

Plasmid pKFN-1000 is a derivative of plasmid pTZ19R (Mead, D. A., Szczesna-Skorupa, E. and Kemper, B., Prot. Engin. 1 (1986) 67–74) containing DNA encoding a synthetic yeast signal-leader peptide. Plasmid pKFN-1000 is described in international patent application no. PCT/DK90/00058. The DNA sequence of 235 bp downstream from the EcoRI site of pKFN-1000 and the encoded amino acid sequence of the synthetic yeast signal-leader is given in SEQ ID No. 3.

Signal-leader-α3(VI): Approx. 0.1 μg of each of the two PCR-fragments described above were mixed. A PCR reaction was performed using 100 pmole each of primers NOR-1478 and NOR-3067 and the following cycle: 94° for 1 min, 50° for 2 min, and 72° for 3 min. After 16 cycles a final cycle was performed in which the 72° step was maintained for 10 min.

The resulting 441 bp fragment was purified by electrophoresis on a 1% agarose gel and then digested with EcoRI and XbaI. The resulting 412 bp fragment was ligated to the 9.5 kb NcoI-XbaI fragment from pMT636 and the 1.4 kb NcoI-EcoRI fragment from pMT636. Plasmid pMT636 is described in International Patent application No. PCT/DK88/00138.

pMT636 is an E. coli—S. cerevisiae shuttle vector containing the Schizosaccharomyces pombe TPI gene (POT) (Russell, P. R., Gene 40 (1985) 125–130), the S. cerevisiae triosephosphate isomerase promoter and terminator, $TPI_P$ and $TPI_T$ (Alber, T., and Kawasaki, G. *J. Mol. Appl. Gen.* 1 (1982), 419–434).

The ligation mixture was used to transform a competent *E. coli* strain (r⁻, m⁺) selecting for ampicillin resistance. DNA sequencing showed that plasmids from the resulting colonies contained the correct DNA sequence for the α3(VI) Kunitz-type domain fused to the synthetic yeast signal-leader gene.

One plasmid pKFN-1745 was selected for further use. The construction of plasmid pKFN-1745 is illustrated in FIG. 1.

The expression cassette of plasmid pKFN-1745 contains the following sequence:

$TPI_P$—KFN1000 signal-leader—α3(VI)—$TPI_T$

The DNA sequence of the 412 bp EcoRI-XbaI fragment from pKFN-1745 is shown in SEQ ID No. 5.

Yeast transformation: *S. cerevisiae* strain MT663 (E2-7B XEll-36 a/α, Δtpi/Δtpi, pep 4-3/pep 4-3) was grown on YPGaL (1% Bacto yeast extract, 2% Bacto peptone, 2% galactose, 1% lactate) to an O.D. at 600 nm of 0.6.

100 ml of culture was harvested by centrifugation, washed with 10 ml of water, recentrifugated and resuspended in 10 ml of a solution containing 1.2M sorbitol, 25 mM Na₂EDTA pH=8.0 and 6.7 mg/ml dithiotreitol. The suspension was incubated at 30° C. for 15 minutes, centrifuged and the cells resuspended in 10 ml of a solution containing 1.2M sorbitol, 10 mM Na₂EDTA, 0.1M sodium citrate, pH =5.8, and 2 mg Novozym® 234. The suspension was incubated at 30° C. for 30 minutes, the cells collected by centrifugation, washed in 10 ml of 1.2M sorbitol and 10 ml of CAS (1.2M sorbitol,10 mM CaCl₂, 10 mM Tris HCl (Tris =Tris(hydroxymethyl)aminomethane pH =7.5) and resuspended in 2 ml of CAS. For transformation, 0.1 ml of CAS-resuspended cells were mixed with approx. 1 µg of plasmid pKFN-1745 and left at room temperature for 15 minutes. 1 ml of (20% polyethylene glycol 4000, 20 mM CaCl₂, 10 mM CaCl₂, 10 mM Tris HCl, pH=7.5) was added and the mixture left for a further 30 minutes at room temperature. The mixture was centrifuged and the pellet resuspended in 0.1 ml of SOS (1.2M sorbitol, 33% v/v YPD, 6.7 mM CaCl₂, 14 µg/ml leucine) and incubated at 30° C. for 2 hours. The suspension was then centrifuged and the pellet resuspended in 0.5 ml of 1.2M sorbitol. Then, 6 ml of top agar (the SC medium of Sherman et al., *(Methods in Yeast Genetics*, Cold Spring Harbor Laboratory (1982)) containing 1.2M sorbitol plus 2.5% agar) at 52° C. was added and the suspension poured on top of plates containing the same agar-solidified, sorbitol containing medium.

Transformant colonies were picked after 3 days at 30° C., reisolated and used to start liquid cultures. One such transformant KFN-1758 was selected for further characterization.

Fermentation: Yeast strain KFN-1758 was grown on YPD medium (1% yeast extract, 2% peptone (from Difco Laboratories), and 3% glucose). A 1 liter culture of the strain was shaken at 30° C. to an optical density at 650 nm of 24. After centrifugation the supernatant was isolated.

The yeast supernatant was adjusted to pH 3.0 with 5% acetic acid and phosphoric acid and applied a column of S-Sepharose Fast Flow (Pharmacia) and equilibrated with 50 mM formic acid, pH 3.7. After wash with equilibration buffer, the HKI-domain was eluted with 1M sodium chloride. Desalting was obtained on a Sephadex G-25 column (Pharmacia) equilibrated and eluted with 0.1% ammonium hydrogen carbonate, pH 7.9. After concentration by vacuum centrifugation and adjustment of pH 3.0 further purification was performed on a Mono S column (Pharmacia) equilibrated with 50 mM formic acid, pH 3.7. After wash with equilibration buffer, gradient elution was carried out from 0–1M sodium chloride in equilibration buffer. Final purification was performed by reverse phase HPLC on a Vydac C4 column (The Separation Group, CA) with gradient elution from 5–55% acetonitrile, 0.1% TFA. The purified product was lyophilized by vacuum centrifugation and redissolved in water.

Aliquots were analyzed by mass PD-mass spectrometry (found: MW 6853,5, calculated: MW 6853–8) and N-terminal amino acid sequencing for 45 Edman degradation cycles confirmed the primary structure of the α3 VI Kunitz-type domain.

Example 2

Production of [R15K, D16A]-α3(VI) and [D16A]-α3(VI) Kunitz-type Domain Analogs from Yeast Strains KFN-1900 and KFN-1901

0.1 µg of the 1.3 kb SphI-BamHI fragment encoding the α3(VI) Kunitz-type domain from plasmid pKFN-1745 was used as a template in two PCR reactions. In the first PCR reaction 100 pmole each of the primers NOR-2022 (GGAGTTTAGTGAACTTGC) (SEQ ID No. 11) and M-753 (GTACCATTTTAATATGAAAGCC(C/T) TGCAAGTTCC) (SEQ ID No. 12) was used. In the second PCR reaction 100 pmole each of the primers NOR-1495 (TAAGTGGCTCAGAATGA) (SEQ ID No. 13) and M-754 ( G G A A C T T G C A ( A / G ) GGCTTTCATATTAAAATGGTAC) (SEQ ID No. 14) was used.

NOR-2022 primes at a position 94 bp downstream of the SphI site. M-753 is complementary to the α3(VI) DNA-sequence position 269–301, SEQ ID No. 5, except for two mismatches. NOR- 1495 primes at a position 561 bp upstream from the BamHI site. M-754 is complementary to M-753.

The PCR reaction was performed in a 100 µl volume using a commercial kit (GeneAmp, Perkin Elmer Cetus) and the following cycle: 95° for 1 min, 50° for 1 min, and 72° for 2 min. After 24 cycles a final cycle was performed in which the 72° step was maintained for 10 min. The PCR products, a 441 bp fragment from the first PCR and a 279 bp fragment from the second, were isolated by electrophoresis on a 2% agarose gel.

Approx. 0.1 µg of each of the two PCR-fragments described above were mixed. A PCR reaction was performed using 100 pmole each of primers NOR-2022 and NOR-1495 and the following cycle: 95° for 1 min, 50° for 2 min, and 72° for 3 min. After 22 cycles a final cycle was performed in which the 72° step was maintained for 10 min.

The resulting 693 bp fragment was purified by electrophoresis on a 1% agarose gel and then digested with EcoRI and XbaI. The resulting 412 bp fragment was ligated to the 2.8 kb EcoRI-XbaI fragment from plasmid pTZ19R (Mead, D. A., Szczesna-Skopura, E., and Kemper, B. *Prot. Engin.* 1 (1986) 67–74).

The ligation mixture was used to transform a competent *E. coli* strain r⁻, m⁺) selecting for ampicillin resistance. By DNA sequencing the following two plasmids encoding the indicated α3(VI) analogs fused to the synthetic yeast signal-leader gene were identified:

| Plasmid | Analog |
|---|---|
| pKFN-1889 | [R15K, D16A]-α3(VI) |
| pKFN-1891 | [D16A]-α3(VI) |

The 412 bp EcoRI-XbaI fragments from these plasmids were used for the construction of the expression plasmids as described in example 1.

Transformation of yeast strain MT-663 as described in example 1 resulted in the following yeast strains:

| Yeast Strain | Analog |
|---|---|
| KFN-1900 | [R15K, D16A]-α3(VI) |
| KFN-1901 | [D16A]-α3(VI) |

Culturing of the transformed yeast strains in YPD-medium, analysis for α3(VI) analogs in the supernatant, and purification was performed as described in example 1.

Example 3

Inhibition of Serine Proteinases by α3 VI Kunitz-type Domain Variants KFN 1900 and 1901

The variants were purified from the yeast culture medium as described in example 1. The concentration of KFN 1651 was determined from the absorbance at 214 nm using aprotinin as a standard. Porcine trypsin was obtained from Novo Nordisk A/S. Human plasmin was obtained from Kabi (Stockholm, Sweden). Human neutrophil cathepsin G and elastase were purified from extracts of PMNs according to the method described by Baugh and Travis, *Biochemistry* 15, 1976, 836–843.

Peptidyl nitroanilide substrates S2251 ans S2586 were obtained from Kabi (Stockholm, Sweden), and S7388 and M 4765 were obtained from Sigma Chemical Co. (St. Louis, Mo., USA).

The serine proteinases were incubated with various concentrations of KFN 1900 or 1901 for 30 minutes. Substrate was then added (0.6 mM) and residual proteinase activity was measured at 405 nm.

KFN 1900 and KFN 1901 were found to be inhibitors of trypsin. $K_i$=50 nM and 355 nM, respectively. KFN 1900 ans 1901 were weak inhibitors of plasmin at 1 μM, but did not inhibit neutrophil elastase or cathepsin G.

We claim:

1. A variant of the C-terminal Kunitz-type protease inhibitor domain of the α3 chain of human type VI collagen, the variant comprising the following amino acid sequence $X^1$ $X^{16}$ Asp Ile Cys Lys Leu Pro Lys Asp $X^2$ Gly $X^3$ Cys $X^4$ $X^5$ $X^6$ $X^7$ $X^8$ $X^9$ Trp Tyr Tyr Asp Pro Asn Thr Lys Ser Cys Ala Arg Phe $X^{10}$ Tyr Gly Gly Cys $X^{11}$ $X^{12}$ $X^{13}$ Glu Asn Lys Phe $X^{14}$ Ser Gln Lys Glu Cys Glu Lys Val Cys Ala Pro $X^{15}$ (SEQ ID NO. 1)

wherein $X^1$ represents Glu;

$X^{16}$ is Thr;

$X^2$ is Glu or Asp;

$X^3$ is Thr;

$X^4$ is Leu or Ile;

$X^5$ is Ala, Gly or Asp;

$X^6$ is Phe;

$X^7$ is Ile;

$X^8$ is Leu;

$X^9$ is Lys;

$X^{10}$ is Val, Leu, Ile or Trp;

$X^{11}$ is Gly;

$X^{12}$ is Ala or Gly;

$X^{13}$ is Asn;

$X^{14}$ is Gly or Ala;

$X^{15}$ is Val;

wherein the variant has protease cathepsin G inhibitory activity.

2. A variant according to claim 1, wherein $X^{10}$ is Val or Trp.

3. A DNA construct comprising a DNA sequence encoding a human Kunitz-type protease inhibitor variant according to claim 1.

4. A recombinant expression vector comprising a DNA construct according to claim 3.

5. A host cell containing a DNA construct according to claim 3.

6. A host cell containing an expression vector according to claim 4.

7. A method of producing a human Kunitz-type protease inhibitor variant according to claim 1, the method comprising culturing a cell according to claim 5 under conditions conducive to the expression of the protein, and recovering the resulting protein from the culture.

8. A method of producing a human Kunitz-type protease inhibitor variant according to claim 1, the method comprising culturing a cell according to claim 6 under conditions conducive to the expression of the protein, and recovering the resulting protein from the culture.

9. A pharmaceutical composition comprising a human Kunitz-type protease inhibitor variant according to claim 1 and a pharmaceutically acceptable carrier or excipient.

* * * * *

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
( A ) LENGTH: 58 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:1:

```
Xaa Xaa Asp Ile Cys Lys Leu Pro Lys Asp Xaa Gly Xaa Cys Xaa Xaa
1               5                   10                  15

Xaa Xaa Xaa Xaa Trp Tyr Tyr Asp Pro Asn Thr Lys Ser Cys Ala Arg
            20                  25                  30

Phe Xaa Tyr Gly Gly Cys Xaa Xaa Xaa Glu Asn Lys Phe Xaa Ser Gln
        35                  40                  45

Lys Glu Cys Glu Lys Val Cys Ala Pro Xaa
    50                  55
```

( 2 ) INFORMATION FOR SEQ ID NO: 2:

( i ) SEQUENCE CHARACTERISTICS:
( A ) LENGTH: 58 amino acids
( B ) TYPE: amino acid
( D ) TOPOLOGY: linear ( i i ) MOLECULE TYPE: protein ( v i ) ORIGINAL SOURCE:
( A ) ORGANISM: synthetic ( x i ) SEQUENCE DESCRIPTION: SEQ ID NO: 2:

```
Glu Thr Asp Ile Cys Lys Leu Pro Lys Asp Glu Gly Pro Cys Lys Ala
1               5                   10                  15
```

```
        Arg  Ile  Ile  Arg  Trp  Tyr  Tyr  Asp  Pro  Asn  Thr  Lys  Ser  Cys  Ala  Arg
                       20                  25                       30

Phe  Val  Tyr  Gly  Gly  Cys  Arg  Ala  Lys  Glu  Asn  Lys  Phe  Lys  Ser  Gln
                  35                       40                       45

Lys  Glu  Cys  Glu  Lys  Val  Cys  Ala  Pro  Val
                  50                       55
```

( 2 ) INFORMATION FOR SEQ ID NO: 3:

( i ) SEQUENCE CHARACTERISTICS:
        ( A ) LENGTH: 235 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: synthetic ( i x ) FEATURE:
        ( A ) NAME/KEY: CDS
        ( B ) LOCATION: 77..235

( x i ) SEQUENCE DESCRIPTION: SEQ ID NO: 3:

```
GAATTCCATT  CAAGAATAGT  TCAAACAAGA  AGATTACAAA  CTATCAATTT  CATACACAAT            60

ATAAACGACC  AAAAGA ATG  AAG  GCT  GTT  TTC  TTG  GTT  TTG  TCC  TTG  ATC         109
                   Met  Lys  Ala  Val  Phe  Leu  Val  Leu  Ser  Leu  Ile
                    1              5                        10

GGA  TTC  TGC  TGG  GCC  CAA  CCA  GTC  ACT  GGC  GAT  GAA  TCA  TCT  GTT  GAG  157
Gly  Phe  Cys  Trp  Ala  Gln  Pro  Val  Thr  Gly  Asp  Glu  Ser  Ser  Val  Glu
               15                       20                       25

ATT  CCG  GAA  GAG  TCT  CTG  ATC  ATC  GCT  GAA  AAC  ACC  ACT  TTG  GCT  AAC  205
Ile  Pro  Glu  Glu  Ser  Leu  Ile  Ile  Ala  Glu  Asn  Thr  Thr  Leu  Ala  Asn
          30                       35                       40

GTC  GCC  ATG  GCT  GAG  AGA  TTG  GAG  AAG  AGA                                 235
Val  Ala  Met  Ala  Glu  Arg  Leu  Glu  Lys  Arg
          45                       50
```

( 2 ) INFORMATION FOR SEQ ID NO: 4:

( i ) SEQUENCE CHARACTERISTICS:
        ( A ) LENGTH: 53 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 4:

```
Met  Lys  Ala  Val  Phe  Leu  Val  Leu  Ser  Leu  Ile  Gly  Phe  Cys  Trp  Ala
 1              5                        10                       15

Gln  Pro  Val  Thr  Gly  Asp  Glu  Ser  Ser  Val  Glu  Ile  Pro  Glu  Glu  Ser
               20                       25                       30

Leu  Ile  Ile  Ala  Glu  Asn  Thr  Thr  Leu  Ala  Asn  Val  Ala  Met  Ala  Glu
          35                       40                       45

Arg  Leu  Glu  Lys  Arg
          50
```

( 2 ) INFORMATION FOR SEQ ID NO: 5:

( i ) SEQUENCE CHARACTERISTICS:
        ( A ) LENGTH: 418 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
    ( A ) ORGANISM: synthetic ( i x ) FEATURE:
    ( A ) NAME/KEY: CDS
    ( B ) LOCATION: 77..409

( i x ) FEATURE:
    ( A ) NAME/KEY: sig_peptide
    ( B ) LOCATION: 77..235

( i x ) FEATURE:
    ( A ) NAME/KEY: mat_peptide
    ( B ) LOCATION: 236..409

( x i ) SEQUENCE DESCRIPTION: SEQ ID NO: 5:

```
GAATTCCATT CAAGAATAGT TCAAACAAGA AGATTACAAA CTATCAATTT CATACACAAT       60

ATAAACGACC AAAAGA ATG AAG GCT GTT TTC TTG GTT TTG TCC TTG ATC          109
               Met Lys Ala Val Phe Leu Val Leu Ser Leu Ile
               -53             -50                     -45

GGA TTC TGC TGG GCC CAA CCA GTC ACT GGC GAT GAA TCA TCT GTT GAG        157
Gly Phe Cys Trp Ala Gln Pro Val Thr Gly Asp Glu Ser Ser Val Glu
            -40             -35                     -30

ATT CCG GAA GAG TCT CTG ATC ATC GCT GAA AAC ACC ACT TTG GCT AAC        205
Ile Pro Glu Glu Ser Leu Ile Ile Ala Glu Asn Thr Thr Leu Ala Asn
        -25             -20                     -15

GTC GCC ATG GCT GAG AGA TTG GAG AAG AGA GAA ACA GAT ATA TGC AAG        253
Val Ala Met Ala Glu Arg Leu Glu Lys Arg Glu Thr Asp Ile Cys Lys
-10                 -5                  1                   5

TTG CCG AAA GAC GAA GGA ACT TGC AGG GAT TTC ATA TTA AAA TGG TAC        301
Leu Pro Lys Asp Glu Gly Thr Cys Arg Asp Phe Ile Leu Lys Trp Tyr
                10                  15                  20

TAT GAT CCA AAC ACC AAA AGC TGT GCA AGA TTC TGG TAT GGA GGT TGT        349
Tyr Asp Pro Asn Thr Lys Ser Cys Ala Arg Phe Trp Tyr Gly Gly Cys
            25                  30                  35

GGT GGA AAC GAA AAC AAA TTT GGA TCA CAG AAA GAA TGT GAA AAG GTT        397
Gly Gly Asn Glu Asn Lys Phe Gly Ser Gln Lys Glu Cys Glu Lys Val
        40                  45                  50

TGC GCT CCT GTG TAATCTAGA                                              418
Cys Ala Pro Val
55
```

( 2 ) INFORMATION FOR SEQ ID NO: 6:

( i ) SEQUENCE CHARACTERISTICS:
        ( A ) LENGTH: 111 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 6:

```
Met Lys Ala Val Phe Leu Val Leu Ser Leu Ile Gly Phe Cys Trp Ala
-53             -50                 -45                 -40

Gln Pro Val Thr Gly Asp Glu Ser Ser Val Glu Ile Pro Glu Glu Ser
            -35             -30                 -25

Leu Ile Ile Ala Glu Asn Thr Thr Leu Ala Asn Val Ala Met Ala Glu
    -20             -15                 -10

Arg Leu Glu Lys Arg Glu Thr Asp Ile Cys Lys Leu Pro Lys Asp Glu
-5                  1                   5                   10

Gly Thr Cys Arg Asp Phe Ile Leu Lys Trp Tyr Tyr Asp Pro Asn Thr
        15                  20                  25
```

```
Lys  Ser  Cys  Ala  Arg  Phe  Trp  Tyr  Gly  Gly  Cys  Gly  Gly  Asn  Glu  Asn
          30                       35                      40

Lys  Phe  Gly  Ser  Gln  Lys  Glu  Cys  Glu  Lys  Val  Cys  Ala  Pro  Val
     45                       50                      55
```

( 2 ) INFORMATION FOR SEQ ID NO: 7:

( i ) SEQUENCE CHARACTERISTICS:
        ( A ) LENGTH: 39 bases
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 7:

GACGGATCTA GATTACACAG GAGCGCAAAC CTTTTCACA                  39

( 2 ) INFORMATION FOR SEQ ID NO: 8:

( i ) SEQUENCE CHARACTERISTICS:
        ( A ) LENGTH: 44 bases
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 8:

GCTGAGAGAT TGGAGAAGAG AGAAACAGAT ATATGCAAGT TGCC            44

( 2 ) INFORMATION FOR SEQ ID NO: 9:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 9:

GTAAAACGAC GGCCAGT                                      17

( 2 ) INFORMATION FOR SEQ ID NO: 10:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 10:

TCTCTTCTCC AATCTCTCAG C                              21

( 2 ) INFORMATION FOR SEQ ID NO: 11:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 11:

GGAGTTTAGT GAACTTGC                                                                 18

( 2 ) INFORMATION FOR SEQ ID NO: 12:

( i ) SEQUENCE CHARACTERISTICS:
        ( A ) LENGTH: 33 bases
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 12:

GTACCATTTT AATATGAAAG CC Y TGCAAGT TCC                                               33

( 2 ) INFORMATION FOR SEQ ID NO: 13:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 13:

TAAGTGGCTC AGAATGA                                                                   17

( 2 ) INFORMATION FOR SEQ ID NO: 14:

( i ) SEQUENCE CHARACTERISTICS:
        ( A ) LENGTH: 33 bases
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 14:

GGAACTTGCA RGGCTTTCAT ATTAAAATGG TAC                                                 33